United States Patent [19]

Yabe

[11] 4,402,313
[45] Sep. 6, 1983

[54] ENDOSCOPE LIGHT SOURCE DEVICE

[75] Inventor: Hisao Yabe, Hachioji, Japan

[73] Assignee: Olympus Optical Co., Ltd., Tokyo, Japan

[21] Appl. No.: 208,066

[22] Filed: Nov. 18, 1980

[30] Foreign Application Priority Data

Nov. 22, 1979 [JP] Japan ................. 54-151613

[51] Int. Cl.³ ............................................. A61B 1/06
[52] U.S. Cl. ...................................................... 128/6
[58] Field of Search ........................................ 128/6, 4

[56] References Cited

U.S. PATENT DOCUMENTS

| | | |
|---|---|---|
| 3,771,099 | 11/1973 | Onse . |
| 4,025,776 | 5/1977 | Cawood et al. ............ 128/6 |
| 4,253,448 | 3/1981 | Terada ....................... 128/6 |
| 4,261,345 | 4/1981 | Yamaguchi ................. 128/6 |

FOREIGN PATENT DOCUMENTS

| | | |
|---|---|---|
| 2216335 | 10/1973 | Fed. Rep. of Germany . |
| 2946372 | 3/1980 | Fed. Rep. of Germany . |
| 2938882 | 4/1980 | Fed. Rep. of Germany . |
| 2041559 | 12/1978 | United Kingdom ......... 128/6 |

*Primary Examiner*—Kyle L. Howell
*Assistant Examiner*—Max F. Hindenburg

*Attorney, Agent, or Firm*—Frishauf, Holtz, Goodman and Woodward

[57] ABSTRACT

An endoscope light source device comprises a light source device body and a connector receptacle rotatably set therein. The connector receptacle is provided with a central through hole for receiving a light guide and cylindrical holes penetrated by contact pins projecting from a base of the connector receptacle. The control pins are connected to the leads extending through the connector receptacle. The leads are connected to signal lines coupled to the signal-generating circuit provided in the light source device body. An electrical connection mechanism is mounted on the signal lines or provided between the respective signal lines and leads to ensure electrical connection between the signal lines and leads. An air-conducting passage is provided in a connection conduit formed in the connector receptacle for communication with the air conducting connection tubes. A fluid-conducting mechanism is provided between the air-conducting-connection tubes and air-conducting passage to ensure communication therebetween, regardless of the rotated position of the connector receptacle. Provision of the rotatable connector receptacle, electrical connection mechanism and fluid-conducting mechanism eliminates the necessity of removing the connector from the endoscope body for each rotation of the endoscope in order to relieve the endoscope from torsion.

26 Claims, 18 Drawing Figures

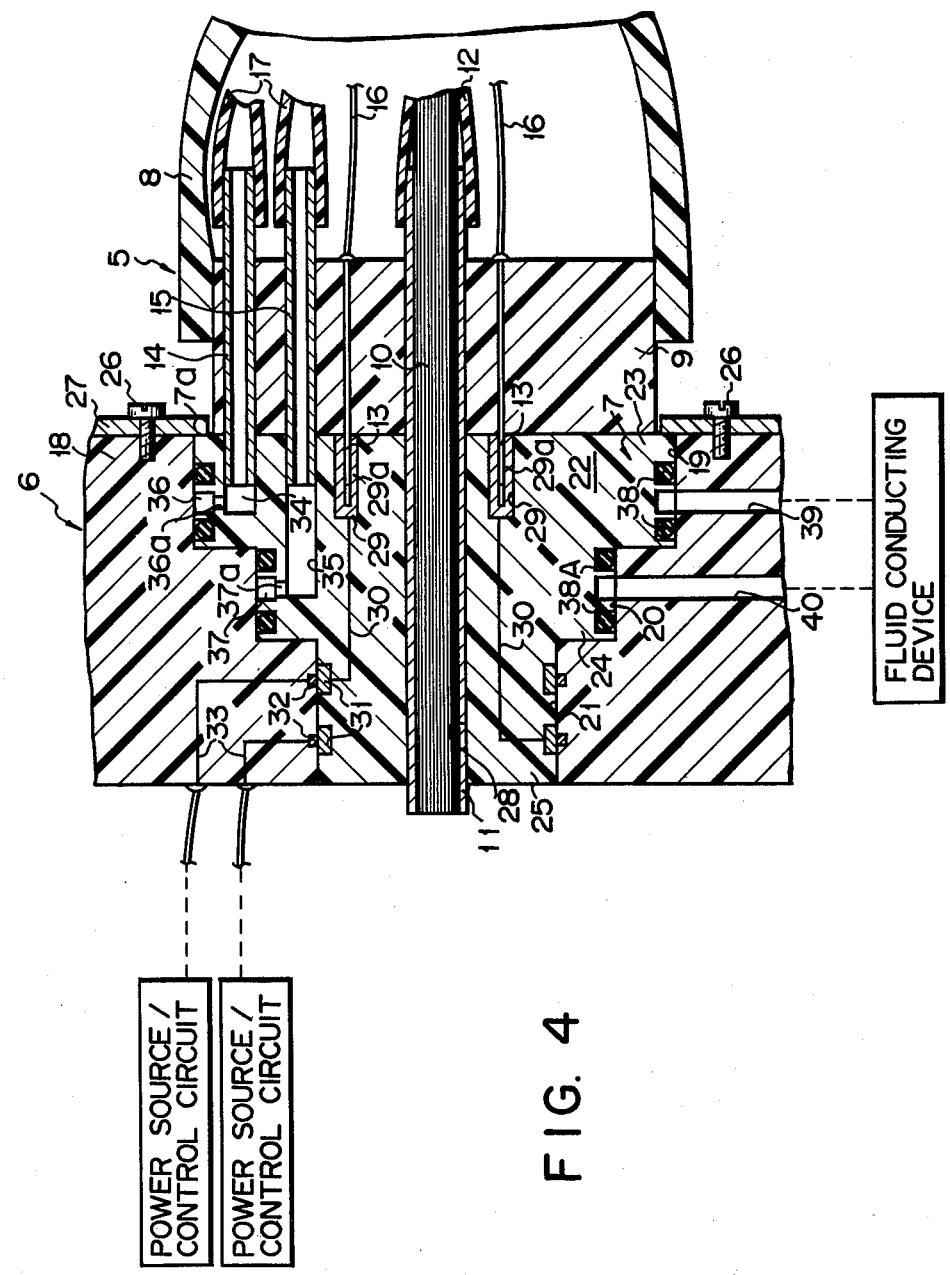
F I G. 4

ENDOSCOPE LIGHT SOURCE DEVICE

BACKGROUND OF THE INVENTION

This invention relates to an endoscope light source device containing a control circuit used to control the operation of a light source for supplying an illumination light to an endoscope, thereby adjusting the supply of the illumination light.

An endoscope and its light source device developed to date generally are shown in FIG. 1. Referring to FIG. 1, an endoscope body 1A comprises a control section 2A, insertion section 3A and flexible umbilical cord (or universal cord) 4A connected to the control section 2A. A connector 5A is fitted to a distal end of the umbilical cord 4A. The connector 5A is detachably fitted into a connector receptacle 7A provided in a light source device 6A.

A light guide tube 8A, air inlet 9A and a plurality of contact pins 10A are projectively provided on the distal end face of the connector 5A. A liquid inlet member 11A is projectively provided on one lateral peripheral wall of the connector 5A. An outlet member 12A is projectively provided on the opposite peripheral wall of the connector 5A. The connector receptacle 7A of the light source device 6A is provided with a through hole 13A for receiving the light guide tube 8A, through hole 14A for receiving an air inlet member 9A and through holes 15A for receiving contact pins 10A. When fitted into the connector receptacle 7A, the connector 5A is rendered non-rotatable relative to the light source device 6A. Where the interior of a complicately bent coeliac cavity such as the large intestine is examined by an endoscope, the endoscope has to be rotated about its axis to a greater extent, as it is inserted more deeply into the coeliac cavity.

Once, however, joined with the connector receptacle 7A of the light source device 6A, the connector 5A fitted to the distal end of the umbilical cord 4A is rendered unrotatable relative to the connector receptacle 7A. Where, therefore, the endoscope is rotated, the umbilical cord 4A is undesirably twisted. Where the insertion of the endoscope into, for example, the large intestine is repeated, the difficulty is presented that the light guide fiber bundle, air and water tubes, and suction tubes, etc. are possibly damaged.

With the conventional endoscope, therefore, the connector 5A is pulled out of the connector receptacle 7A to release the umbilical cord 4A from twisting, and thereafter the connector 5A is again inserted into the receptacle 7A. At this time, the tubes connected to the liquid inlet member 11A and outlet member 12A also have to be pulled out, undesirably resulting in the suspension of coeliac examination during the interior.

It is accordingly the object of this invention to provide an endoscope light source device, wherein a connector receptacle connected to a connector of an endoscope is rotatably provided in a light source device, thereby preventing the twisting of an umbilical cord caused by the rotation of the endoscope, and also the damage of an illumination optical fiber bundle and tubes inserted into the umbilical cord.

SUMMARY OF THE INVENTION

To attain the above-mentioned object, this invention provides an endoscope light source device which comprises a light source device body and a connector receptacle rotatably set therein. The connector receptacle is provided with a central through hole for receiving a light guide and through holes for receiving a plurality of contact pins projecting from a connector base. The contact pins are connected to leads provided in the connector receptacle. The leads are coupled to signal lines connected to signal-generating circuits of the light source device body. Provided on the signal lines or between the signal lines and leads are electric connection means to effect electrical connection between the signal lines and leads, regardless of the rotated position of the connector receptacle. An air passage is provided in a connector conduit provided in the connector receptacle for communication with an air-conduction connection tube. Provided between the air-conducting connection tube and air passage is a fluid-conducting means for effecting communication between the air-conducting air connection tube and air passage, regardless of the rotated position of the connector receptacle.

Provision of the rotatable connector receptacle, electric connection devices and fluid-conducting device completely eliminates the necessity of removing the connector from the endoscope body for each rotation of the endoscope in order to relieve its twisting.

BRIEF DESCRIPTION OF THE DRAWINGS

FIG. 4 is a longitudinal cross sectional view of a main part of an endoscope light source device according to one embodiment of the invention;

DETAILED DESCRIPTION

Figure 1:
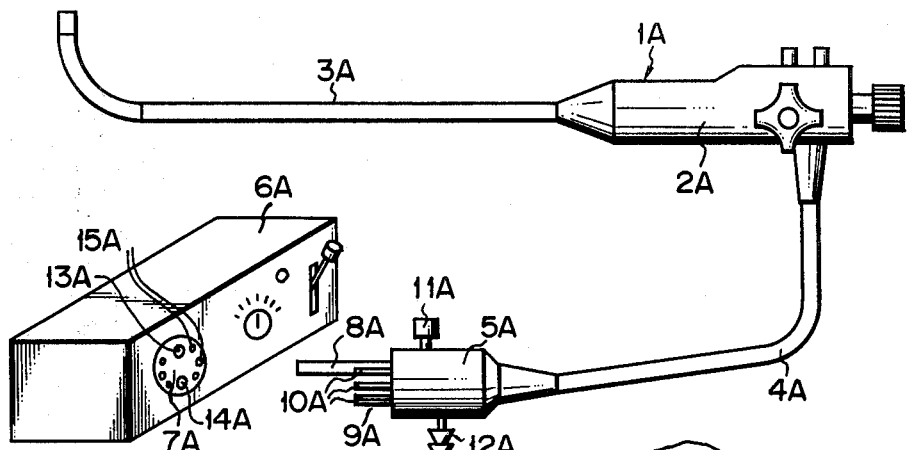
FIG. 1 is an oblique view of the whole of a known endoscope light source device, also showing an endoscope.
Figure 2:
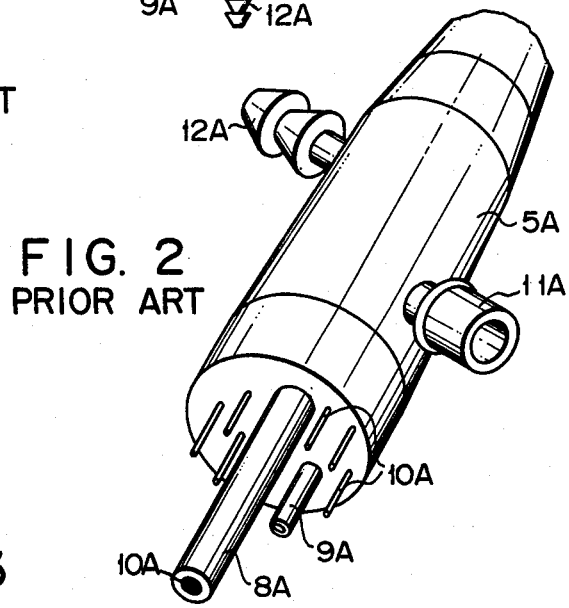
FIG. 2 is an oblique view of a known endoscope connector.
Figure 3:
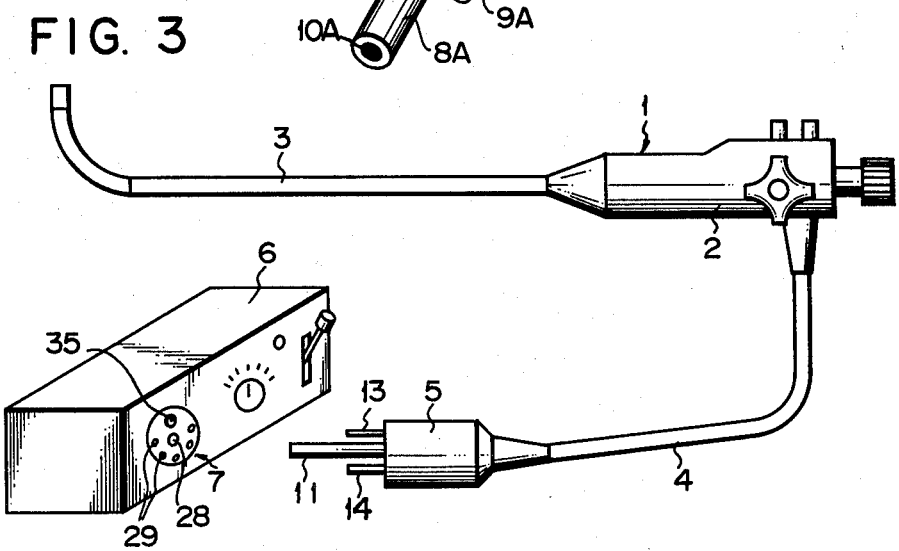
FIG. 3 is an oblique view of the whole of an endoscope light source device embodying this invention, also showing an endoscope.

FIGS. 3 and 4 show an endoscope light source device according to a first embodiment of this invention. An endoscope body 1 comprises a control section 2, flexible insertion section 3 and flexible umbilical cord (or universal cord) 4 connected to one lateral side of the control section 2. The later described endoscope connector 5 is connected to the distal end of the umbilical cord 4. The connector 5 is detachably connected to the later described connector receptable 7 of a light source device body 6.

As seen in FIG. 4, the endoscope connector 5 comprises a cylindrical connector cover 8, the distal end opening of which is fitted with a disc-shaped base 9 prepared from electrically insulating material such as epoxy resin. A light guide tube 11 enclosing a light guide 10 formed of an illumination optical fiber bundle penetrates central part of the base 9, and projects outward from the front end face of the base 9.

The light guide 10 enclosed by a protective tube 12 passes through the umbilical cord 4 to the distal end face of the endoscope body 1. The protective tube 12 of the light guide or illumination optical fiber bundle 10 is connected to a proximal end of the light guide tube 11 in the connector 5 as seen in the right-hand side of FIG. 4.

Contact pins 13 surrounding the light guide tube 11 axially penetrate the base 9, and project outward from the distal end face of the base 9. A pair of air-conducting tubes 14, 15 axially penetrate the base 9 at a point near the outer periphery of the base 9 and project outward from the front or distal end of the base 9.

The proximal end of each of the contact pins 13 is connected to the corresponding end of a signal line 16 coupled to an electric circuit of the endoscope body 1. The air-conducting tubes 14, 15 are respectively connected at the proximal end to air-conducting tubes 17. The signal lines 16 and air-conducting tubes 17 pass through the umbilical cord 4 into the endoscope body 1.

Description is now given of the connector receptacle 7 of the endoscope light source device according to the first embodiment of this invention. A front panel 18 of the light source device body 6 is provided with a stepped fitting cavity 22 consisting of a larger diameter cylindrical region 19, medium diameter cylindrical region 20 and smaller diameter cylindrical region 21 arranged from the front part to the rear part of the light source device body 6.

The connector receptacle 7 comprises a larger diameter cylindrical portion 23, medium diamter cylindrical portion 24 and smaller diameter cylindrical portion 25 whose outer peripheral walls are made complementary to the inner peripheral walls of the larger, medium and smaller diameter cavity regions 19, 20, 21. Engagement of the larger, medium and smaller portions 23, 24, 25 with the complementary cavity regions 19, 20, 21 of the fitting cavity 22 enables the connector receptacle 7 to be rotatably set in the fitting cavity 22.

The front peripheral edge 7a of the connector receptacle 7 is held by a ring-shaped keep plate 27 fixed to the front panel 18 by set screws 26, thereby preventing the connector receptacle 7 from falling off the fitting cavity 22. The connector receptacle 7 is provided at the center with a through hole 28 penetrated by the light guide 10 in the light guide tube 11 of the connector 5. Cylindrical axial connection holes 29 for receiving the contact pins 13 surround the through hole 28, and are formed in the connector receptacle 7 in a state opened at the front end face of the connector receptacle 7. Fixed in each of the connection holes 29 is a hollow cylindrical pin receptacle 29a which is prepared from electrically conductive material such as copper and used to receive the corresponding contact pin 13.

The pin receptacles 29a are connected by first electrical connecting leads 30 to respective contact rings 31 which are prepared from electrically conductive material such as copper and fitted around the outer peripheral wall of the smaller diameter portion 25 of the connector receptacle 7. Contact strips 32 prepared from electrically conductive material such as copper are embedded in the inner peripheral wall of the smaller diameter section 21 of the fitting cavity 22 for contact with the respective contact rings 31. Second electrical connecting leads 33 extending from the contact strips 32 pass through the front panel 18 to, for example, a power source and/or a photographic electrical control circuit provided in the light source device body 6. Not only those portions of the front panel 18 which surround the connector receptacle 7 and are penetrated by the leads 33, but also the connector receptacle 7 and connector base 9 are prepared from electrically insulating plastic material such as epoxy resin to suppress the leakage of electric current from the leads 30, 33, contact rings 31, contact strips 32 and signal lines.

Axially extending connection conduits 34, 35 respectively communicating with the air-conducting tubes 14, 15 are formed in the connector receptacle 7. The connection conduits 34, 35 further respectively communicate with annular air-conducting grooves 36, 37 formed in the outer peripheral walls of the larger diameter portion 23 and medium diameter section 24 through radially extending holes 36a, 37a. The annular grooves 36, 37 and radially extending holes 36a, 37a comprise an air-conducting means. Both lateral edges of the air-conducting groove 36 are fitted with O-rings 38. Similarly, both lateral edges of the air-conducting groove 37 are fitted with O-rings 38A. Application of the O-rings 38, 38A provides an airtightness between the fitting cavity 22 and the air-conducting annular groove 36, as well as between the fitting cavity 22 and the air-conducting annular groove 37. An air passage 39 communicating with the air-conducting groove 36 is provided in the larger diameter section 19 of the fitting cavity 22. An air passage 40 communicating with the air-conducting groove 37 is provided in the medium diameter section 20 of the fitting cavity 22. The air passages 39, 40 are respectively connected to a fluid conducting device (not shown) in detail, thereby effecting the supply of air and water into a coeliac cavity (for example, the large intestine) and the withdrawal of a coeliac fluid.

In operation, where the insertion section 3 of the endoscope body 1 is pushed into a twisted coeliac cavity such as the large intestine while being rotated about the axis of the insertion section 3, the umbilical cord 4 connected to the control section 2 of the endoscope body 1 undergoes a twisting force, applying a torsional moment to the connector 5 of the umbilical cord 4. Since the connector receptacle 7 coupled to the connector 5 is rotatable relative to the fitting cavity 22 of the light source device body 6, both connector 5 and connector receptacle 7 are jointly rotated by the above-mentioned torsional moment. Therefore, the umbilical cord 4 is prevented from being actually twisted, thereby preventing the damage of the parts in the umbilical cord 4 as well as the inserted illumination optical fiber bundle 10 and air-conducting tubes 17.

The light guide tube 11 disposed at the center of the connector receptacle 7 always faces a light source, thereby effecting the transmission of an illumination light even when both connector 5 and connector receptacle 7 are jointly rotated. The contact rings 31 are respectively slidably pressed against the contact strips 32, always ensuring electrical conduction. Further, the air passages 39, 40 communicate with the respective air-conducting grooves 36, 37, allowing for the continuation of the supply of power, air and water and the withdrawal of a coeliac fluid.

Figure 5:
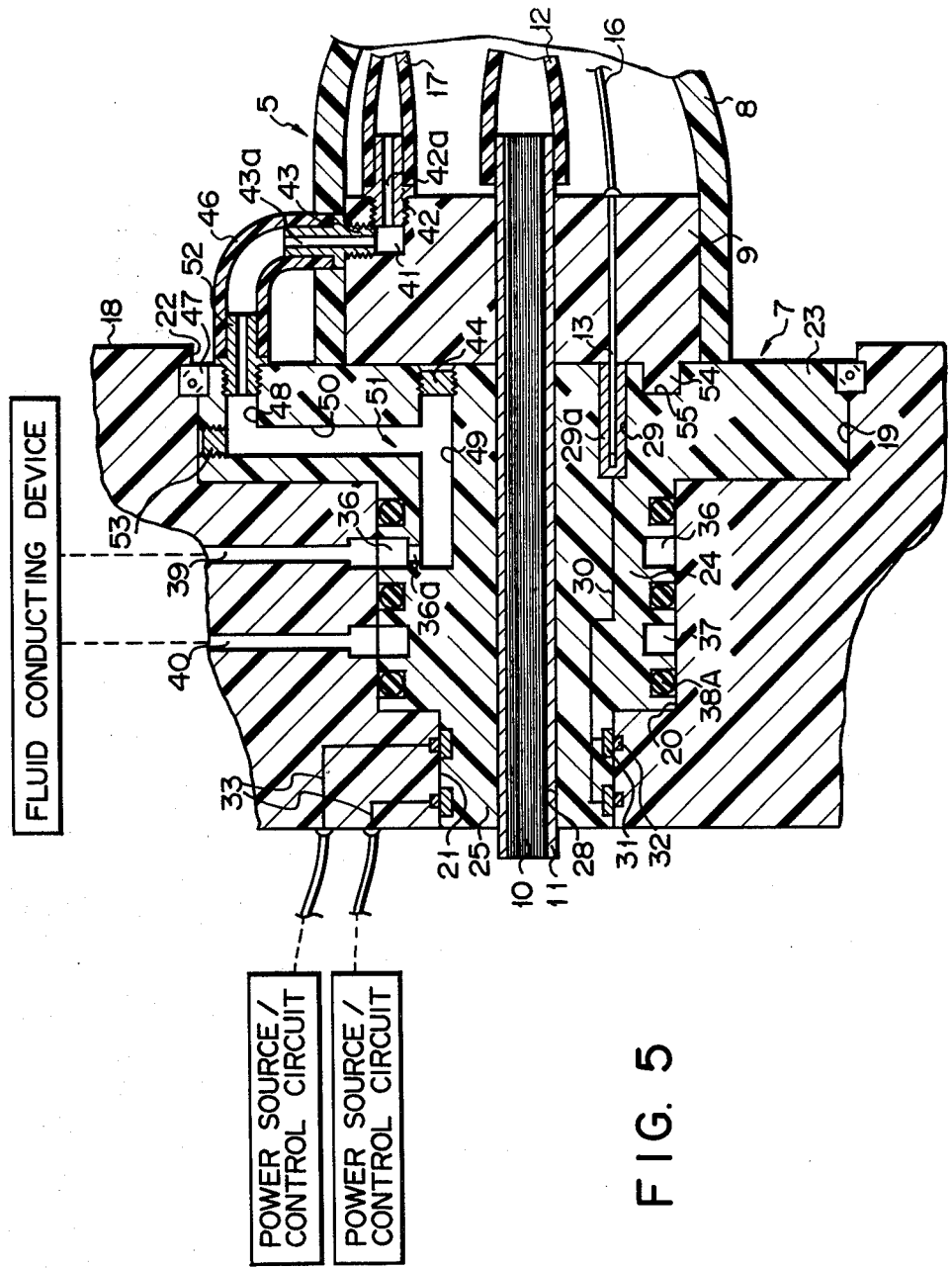
FIG. 5 is a longitudinal cross sectional view of a main part of an endoscope light source device according to another embodiment of the invention.

Description is now given with reference to FIG. 5 of an endoscope light source device according to a second embodiment of this invention. A base 9 of a connector 5 has an air passage 41 consisting of an air-conducting hole 42a extending axially of the connector 5 and an air-conducting hole 43a extending radially of the connector 5. The air-conducting hole 42a is formed in a fitting 42 threadedly engaged with the base 9 on its front side. The air-conducting hole 43a is formed in a fitting 43 threadedly engaged with the base 9 on its outer peripheral wall. The projecting end of the fitting 42 is connected to the end of the air-conducting tube 17. The projecting end of the fitting 43 is connected to the end of the connection tube 46.

The connector receptacle 7 is rotatably supported in the fitting cavity 22 provided in the front panel 18 of the light source device body 6 by means of a bearing 47. Formed in the connector receptacle 7 is an air passage 51 consisting of a first air-conducting hole 48 and a second air-conducting hole 49 both extending axially of the connector receptacle 7 and another air-conducting hole 50 extending radially of the connector receptacle 7 for communication with the first and second air-conducting holes 48, 49. An air-conducting fitting 52 is threadedly engaged with the first air-conducting hole 48. The other ends of the connection tube 46 of the connector 5 is connected to the air-conducting fitting 52. The front end of the second axially extending air-conducting hole 49 and the outer end of the radially extending air-conducting hole 50 are hermetically sealed by the corresponding plugs 44, 53. The opposite end of the second axially extending air conducting hole 49 communicates with an air-conducting groove 36 through a connection hole 36a. The air passage 41 of the connector 5 communicates with an air passage 39 through the connection tube 46 and air passage 51.

A projection 54 is formed on the front face of the connector base 9, and fitted into a cavity 55 which is formed in the front face of the connector receptacle 7 with a shape complementary to the projection 54. Engagement between the projection 54 and cavity 55 enables the rotation of the connector 5 to be reliably transmitted to the connector receptacle 7. This connector receptacle 7 which is rotatably supported by the bearing 47 prevents the shaking of the connector recepacle 7.

Where, with the second embodiment, another air-conducting tube is provided in addition to the air-conducting tube 17 as in the first embodiment, elements corresponding to the air-conducting fittings 42, 43, 52, connection tube 46 and air-conducting passage 51 are provided. In this case, it is possible to connect said another air-conducting tube to the air passage 40.

The other parts of the second embodiment are operated in substantially the same manner with the same effect as those of the first embodiment, description thereof being omitted.

Figure 6:
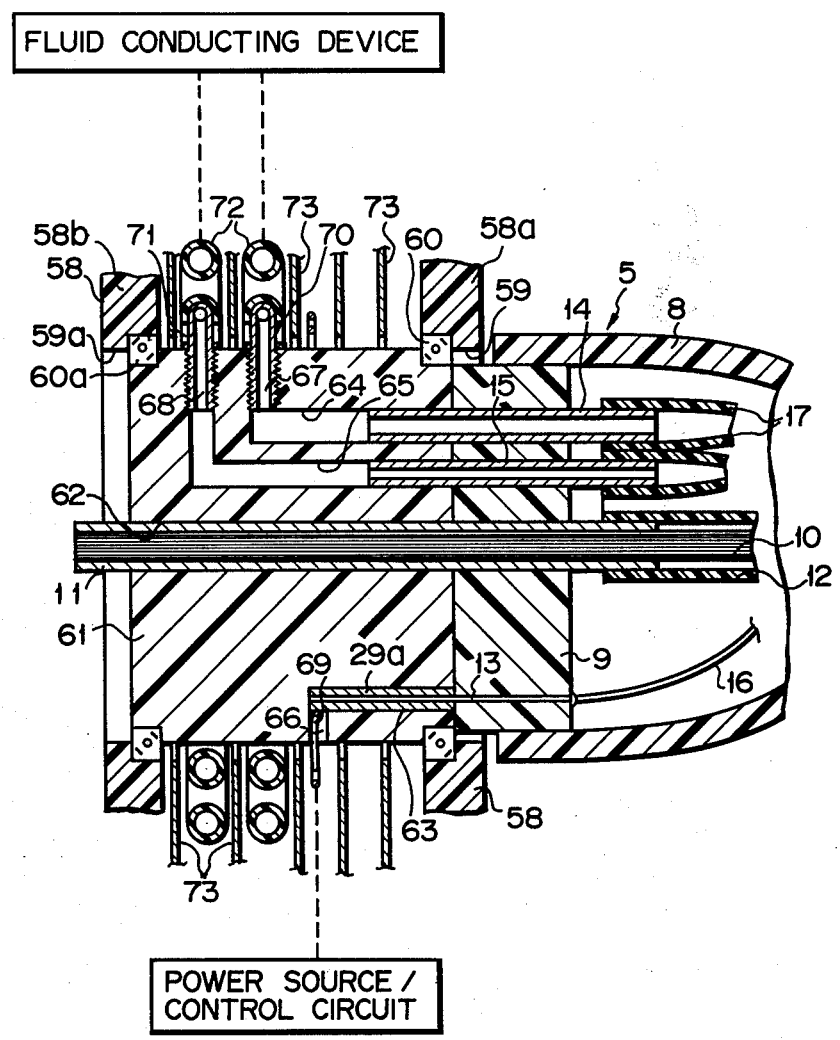
FIG. 6 is a longitudinal cross sectional view of a main part of an endoscope light source device according to still another embodiment of the invention.
Figure 7:
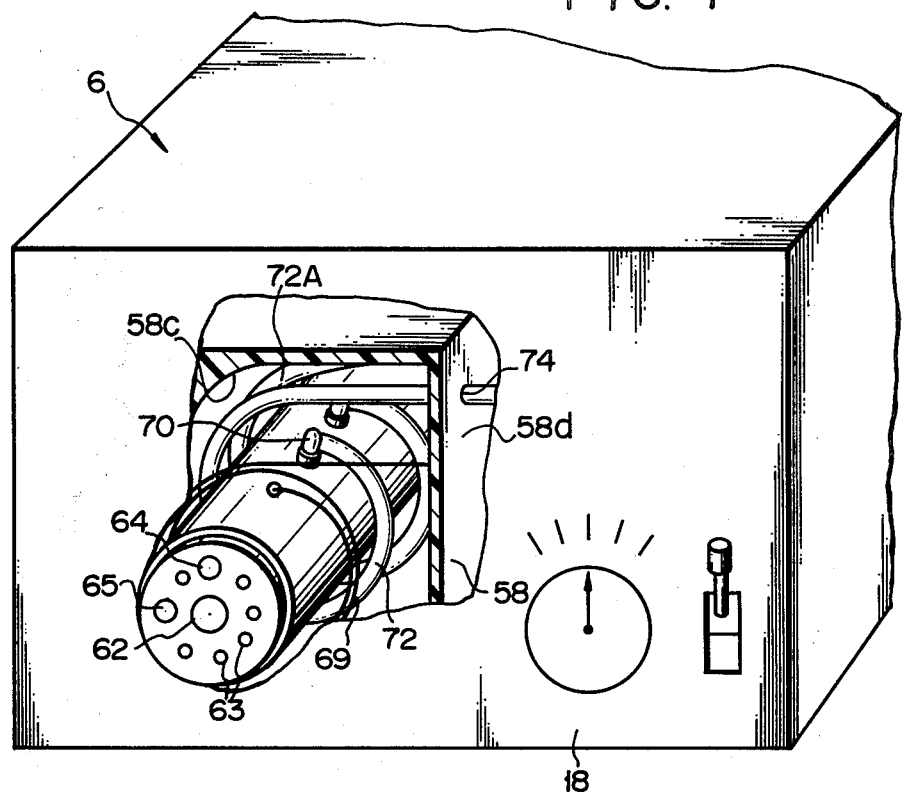
FIG. 7 is an oblique view of a box according to one embodiment of the invention, also showing the main part of the endoscope light source device.
Figure 8:
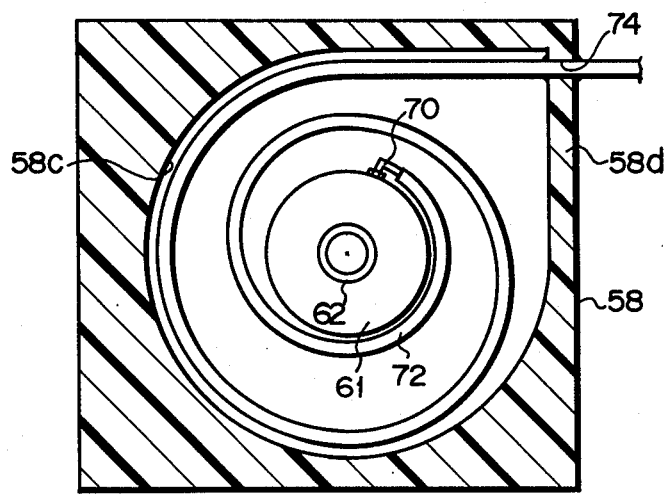
FIG. 8 is a cross sectional view of the box of FIG. 6.

Description is now given with reference to FIGS. 6 to 8 of an endoscope light source device according to a third embodiment of this invention.

A box 58 is provided in the light source device body 6 in a state closely facing the front panel 18 thereof. A concentric support hole 59 is formed in the front wall 58a of the box 58. A concentric hole 59a is formed in the rear wall 58b of the box 58. The box 58 defines a cavity for receiving a connector receptacle 61.

The inner walls of the support holes 59, 59a are fitted with corresponding bearings 60, 60a, thereby rotatably supporting a cylindrical connector receptacle 61. Provided in the cylindrical connector receptacle 61 are a central through hole 62 penetrated by a light guide 10 in a light guide tube 11, cylindrical axial connection holes 63 which extend axially of the connector receptacle 61 and fitted with hollow cylindrical pin receptacles 29 into which contact pins 13 are inserted, and axially extending connection conduits or passages 64, 65 into which the corresponding ends of air-conducting tubes 14, 15 are inserted. The innermost ends of the connection holes 63, and connection conduits or passages 64, 65 communicate with the outside of the connector receptacle 61 through the corresponding passages 66, 67, 68 which extend radially of the connector receptacle 61 and are open at the outer peripheral wall of the connector receptacle 61.

Electrical connecting leads 69 connected to the rear ends of the pin receptacles 29a are drawn out of the connector receptacle 61 through the passage 66 and loosely wound about the outer peripheral wall of the connector receptacle 61. Air-conducting fittings 70, 71 threadedly engaged at one end with the outer peripheral wall of the connector receptacle 61 have the corresponding internal air passages 67, 68, and are bent at right angles substantially at midpoint to take an L-shape (FIG. 8). Air-conducting tubes 72 are connected at one end to the aforesaid one end of each of the air-conducting fittings 70, 71. The air-conducting tubes 72 are connected at the other end to fluid conducting means such as an air or water pump and/or suction device. Like the signal lines 69, the air-conducting tubes 72 are loosely wound about the outer peripheral wall of the connector receptacle 61. The electrical connecting leads 69 and air-conducting tubes 72 are spaced from each other axially of the connector receptacle 61 at a proper distance by a plurality of partition boards 73 which are arranged in the box 58 and each provided with a hole penetrated by the connector receptacle 61. Therefore, the leads 69 and air-conducting tubes 72 are prevented from being entangled with each other. An inner peripheral wall of a portion 58c (FIG. 7) of the box 58 is made into a semicircular form extending along the outer peripheral wall of the connector receptacle 61. That portion 58d of the inner wall of the box 58 which faces the aforesaid portion 58c are provided with outlets 74 through which the signal lines 69 and air-conducting tubes 72, 72A are drawn out (for convenience, FIG. 7 only shows an outlet for the air-conducting tube 72).

When the connector 5 undergoes a twisting force, the connector receptacle 61 is rotated. Where the rotation is made clockwise of FIG. 8, the rolls of the electrical connecting leads 69 and those of the air-conducting tubes 72 increase in diameter. Where the rotation is made counterclockwise of FIG. 8, the rolls of the leads 69 and those of the air-conducting tubes 72 decrease in diameter. In either case, a sufficient margin is allowed in the length of the leads 69 and air-conducting tubes 72, and also in the capacity of the box 58. Therefore, the connector receptacle 61 is not obstructed in rotation.

Figure 9:
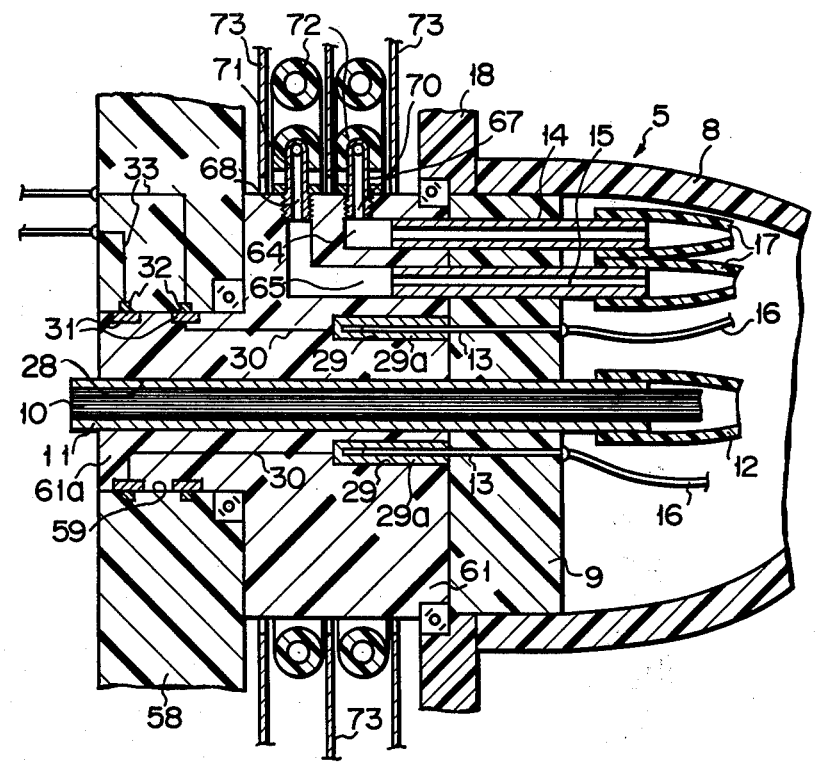
FIG. 9 is a longitudinal cross sectional view of a main part of an endoscope light source device according to a further embodiment of the invention.

Description is now given with reference to FIG. 9 of an endoscope light source device according to a fourth embodiment of this invention. As in the third embodiment, the air-conducting tubes 72 are wound about the outer peripheral wall of the connector receptacle 61. The signal lines 16 are connected to a signal-generating circuit provided in the light source device body 6 by means of first electrical connecting leads 30 extending through the connector receptacle 61, metal contact rings 31 mounted on the outer peripheral wall of the smaller diameter portion 61a of the connector receptacle 61, contact strips 32 embedded in the inner peripheral wall of the support hole (fitting cavity) 59 formed in the box 58, second electrical connecting and leads 33 extending from the contact strips 32 through the box 58 and light source device body 6. The parts of the fourth embodiment the same as those of the preceding embodiments are denoted by the same numerals, description thereof being omitted. With the fourth embodiment of FIG. 9 arranged as described above, the box 58 is more compact than that of the third embodiment.

Figure 10:
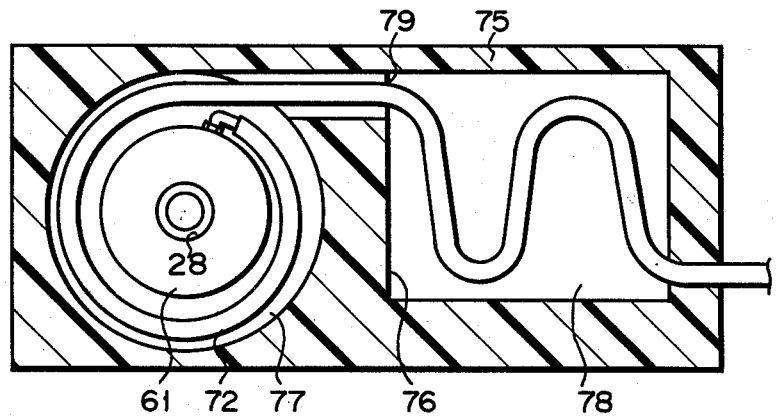
FIG. 10 is a cross sectional view of a box according to another embodiment of the invention.

Description is now given with reference to FIG. 10 of a fifth embodiment of this invention. A box 95 used in this fifth embodiment is modified from those of the third and fourth embodiments. The box 75 of the fifth embodiment shown in FIG. 10 has a rectangular cross section. A partition wall 76 integrally formed in the longitudinally intermediate part of the box 75 divides the box 75 into a chamber 77 for holding a connector receptacle 61 and an adjustment chamber 78. This chamber 78 is used to control the extent to which the air-conducting tubes 72 are drawn out of box 75. A hole 79 for effecting communication between the connector receptacle holding chamber 77 and adjustment chamber 78 is provided in the partition wall 76. The air-conducting tubes 72 wound about the connector receptacle 61 pass through the hole 79 into the adjustment chamber 78 at one end, and are drawn out at the other end of the chamber 78.

Where the connector receptacle 61 is rotated clockwise of FIG. 10, the air-conducting tubes 72 wound about the connector receptacle 61 are progressively drawn out through the hole 79 into the adjustment chamber 78. Conversely where the connector receptacle 61 is rotated counterclockwise of FIG. 10, the air-conducting tubes 72 held in the adjustment chamber 78 are pulled out through the hole 79 to be wound about the connector receptacle 61. Therefore, the connector receptacle 61 can be smoothly rotated in either direction without the mutual entanglement of the air-conducting tubes.

Figure 11:
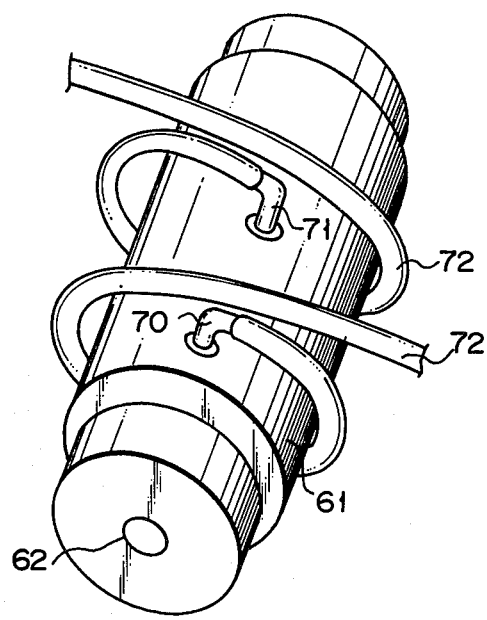
FIGS. 11 to 13 are oblique views of the various forms of the main part of the invention according to different embodiments.

Description is now given with reference to FIG. 11 of an endoscope light source device according to a sixth embodiment of this invention. FIG. 11 illustrates the modified manner in which air-conducting fittings 70, 71 connected to the air-conducting tubes 72 are mounted on the connector receptacle 61. Namely, with the sixth embodiment, the air-conducting fittings 70, 71 are attached to the connector receptacle 61 with the respective outlet portions of the fittings 70, 71 disposed in opposite directions as viewed circumferentially of the connector receptacle 61. As a result, one of the air-conducting tubes 72 is wound clockwise about the connector receptacle 61, whereas the other of the air-conducting tubes 72 is wound counterclockwise about the connector receptacle 61. This arrangement causes the restoring forces of the respective air-conducting tubes 72 to be cancelled by each other, thereby enabling the connector receptacle 61 to be smoothly rotated even when not receiving an appreciably great rotation moment.

Figure 12:
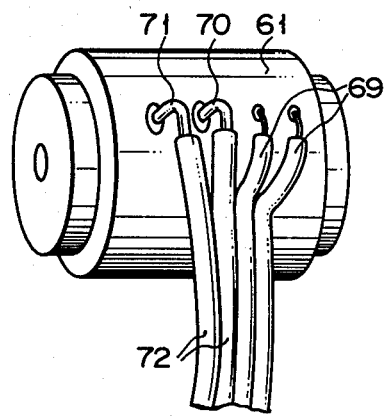
Figure 13:
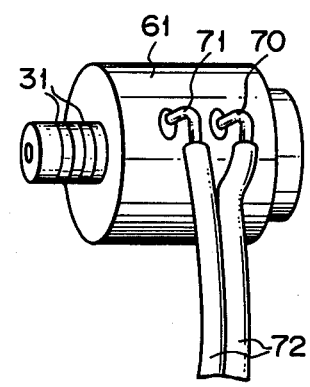

Description is now given with reference to FIG. 12 of an endoscope light source device according to a seventh embodiment of this invention. A plurality of electrically insulative tubes holding signal lines 69 and a plurality of air-conducting tubes 72 are tightly juxtaposed to each other into a flat block. FIG. 13 shows an eighth embodiment of this invention, in which all the air-conducting tubes 72 are tightly juxtaposed to each other. The arrangements of the seventh and eighth embodiments eliminate the necessity of providing a partition wall 73 in the box 58 as in the third and fourth embodiments, and further prevent entanglement between the signal lines 69 and air-conducting tubes 72.

Figure 14:
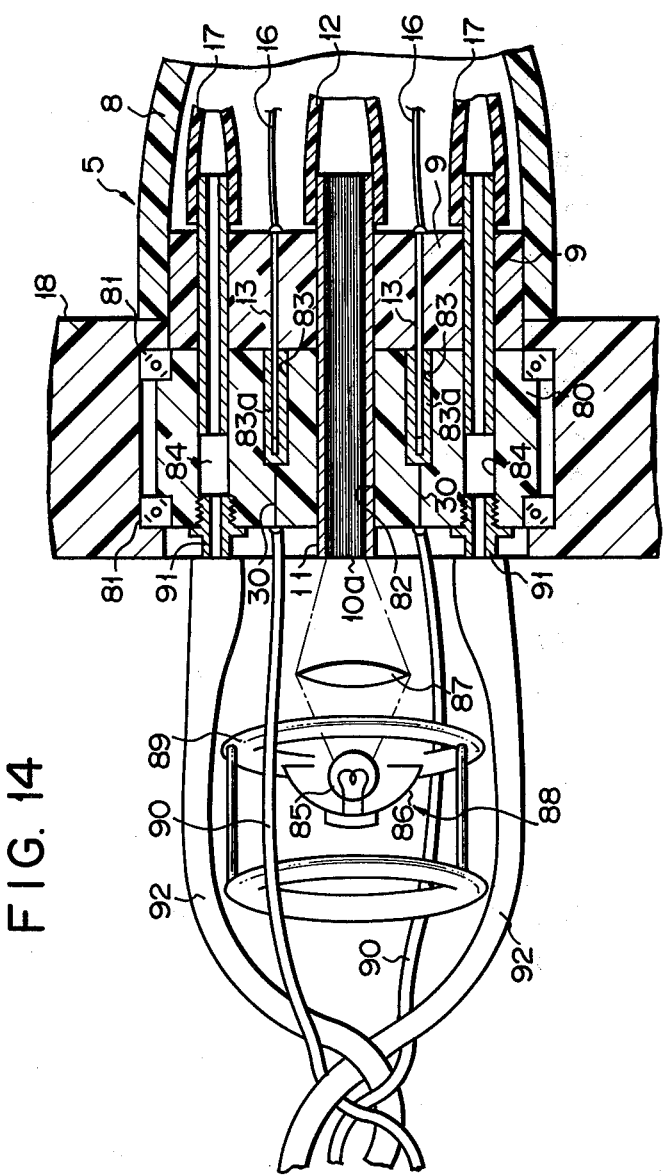
FIG. 14 is a longitudinal cross sectional view of a main part of an endoscope light source device according to a still further embodiment of the invention.

Description is now given with reference to FIG. 14 of an endoscope light source device according to a ninth embodiment of this invention. The connector receptacle 80 of this ninth embodiment has substantially the same arrangement as that of previously described embodiments, description thereof being omitted. The front and rear edges of the connector receptacle 80 are rotatably supported on the front panel 18 by means of bearings 81. Axially extending connection holes 83 are formed in the connector receptacle 80 in parallel with each other on both sides of a central through hole 82 penetrated by a light guide 10 in a light guide tube 11. Axially extending connection conduits 84 are also formed in the connector receptacle 80 similarly in parallel with each other on both sides of the central through hole 82. A light source unit 88 comprising a lamp 85, reflector 86 and compound lens 87 is provided on the same optical axis as that of the light guide 10 in a state spatially facing a light-receiving end face 10a of the light guide 10. A ring protective member 89 encloses the lamp 85 and reflector 86. Electrical connecting leads connected to control signal lines 90 on the rear side of the connector receptacle and 80 are connected at their respective other ends to hollow cylindrical pin receptacles 83a in respective connection holes 83. The pin receptacles 83a are prepared from an electrically conductive metal such as copper and are fixed in the contact holes 83 to receive contact pins 13 projecting from the base of the connector 5. Air-conducting fittings 91 projecting inward from the rear side of the connector receptacle 80 are threadedly engaged with the connection conduits 84, and also connected to air-conducting tubes 92 coupled to pumps for supplying air and water and a device for draining a coeliac fluid. The control signal lines 90 enclosed by electrically insulative tubes and air-conducting tubes 92 extend toward the rear side of the connector receptacle 80 and are loosely knitted together on the rear side of the light source unit 88.

Where the control signal lines 90 and air-conducting tubes 92 are knitted together more tightly by the rotation of the connector receptacle 80, the torsion of the endoscope resulting from the rotation of the connector receptacle 80 can be more effectively absorbed. Since, at this time, the light source unit 88 is enclosed in the protective guard 89, neither control signal lines 90 nor air-conducting tubes 92 interfere with or damage the light source unit 88 or obstruct a light path.

Figure 15:
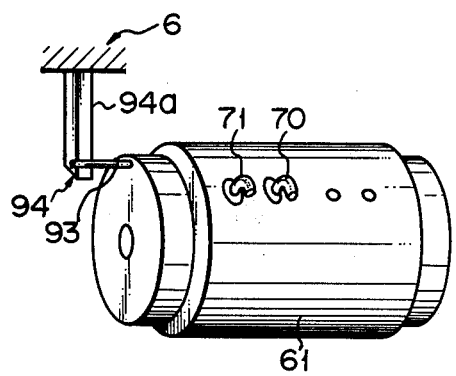
FIGS. 15 and 16 are oblique views of the parts of a rotation-control device according to one embodiment of the invention.

Description is now given with reference to FIG. 15 of an endoscope light source device according to a tenth embodiment. This tenth embodiment is constructed by adding a rotation control mechanism 94 to the third embodiment of FIG. 6. This rotation control mechanism 94 comprises an axially extending pin 93 projectively provided on the rear side of the connector receptacle 61 at an eccentric point relative thereto and a rotation control member 94a which extends radially of the connector receptacle 61, is fixed to the light source device body 6 and is engageable with the pin 93.

Figure 16:
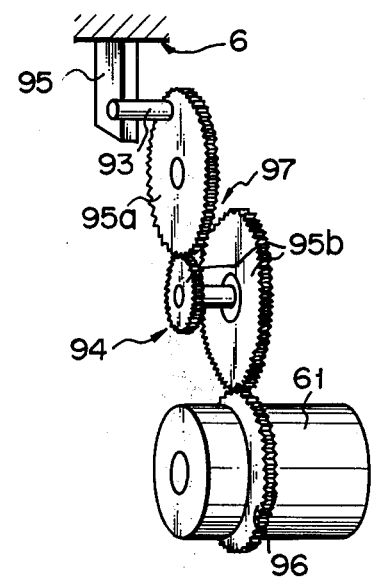

Description is now given with reference to FIG. 16 of an endoscope light source device according to an eleventh embodiment of this invention. This eleventh embodiment is constructed by adding a reduction gear mechanism 95 to the tenth embodiment. The reduction gear mechanism 95 comprises a gear 95a fitted with an eccentrically disposed pin 93, gear 96 disposed concentrically with the connector receptacle 61 and an intermediate gear assembly 95b interposed between the gears 95a and 96. A rotational speed reduced by the reduction gear mechanism 95 is transmitted to the pin 93.

Application of the rotation control mechanism 94 used with the tenth and eleventh embodiment controls the extent to which the connector receptacle 61 is rotated, thereby preventing the signal lines 69 and air-conducting tubes 72 from being damaged.

Figure 17:
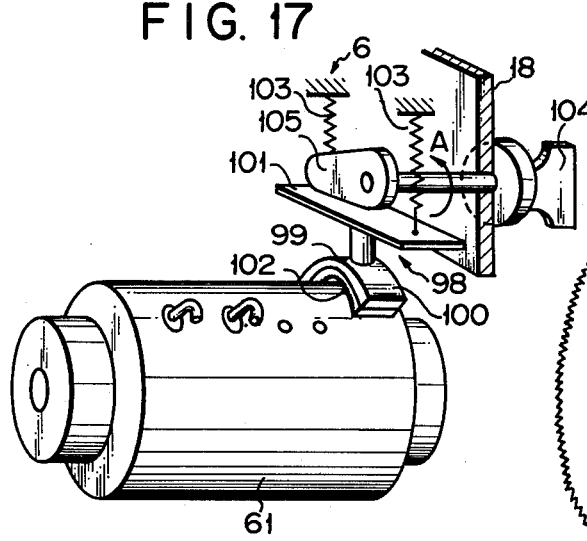
FIG. 17 is an oblique view of a brake used with the endoscope light source device of the invention.

Description is now given with reference to FIG. 17 of an endoscope light source device according to a twelfth embodiment of this invention. This twelfth embodiment is constructed by attaching a brake mechanism 98 to the connector receptacle 61.

With the brake mechanism 98, a brake body 99 comprises an arcuate shoe 100 bent in conformity to the curvature of the outer periphery of the connector receptacle 61 and a plate-shaped follower 101 integrally formed with the arcuate shoe 100. That side of the arcuate shoe 100 which contacts the outer peripheral wall of the connector receptacle 61 is fitted with a pad 102 prepared from elastic material such as rubber.

Tension springs 103 are stretched between the inner wall of the light source device body 6 and plate-shaped follower 101 to urge the brake body 99 away from the connector receptacle 61. Engaged with the upper surface of the plate-shaped follower 101 is a cam 105 rotated by a knob 104 penetrating the front panel 18 of the light source device body 6.

In a first position, as indicated in FIG. 17, the brake body 99 remains lifted by the tension springs 103, rendering the connector receptacle 61 freely rotatable. Where, however, the knob 104 is rotated about 90° in the direction of an indicated arrow A, the brake body 99 is pushed downward by the cam 105, causing the shoe 100 to be pressed against the connector receptacle 61 with the pad 102 interposed therebetween, thereby keeping the connector receptacle 61 unrotatable. When, therefore, connected to the connector 5, the connector receptacle 61 is prevented from being unexpectedly rotated.

Figure 18:
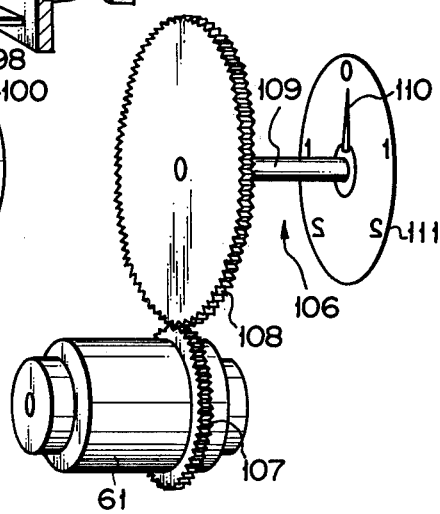
FIG. 18 is an oblique view of a rotation control mechanism according to another embodiment of the invention.

Description is now given with reference to FIG. 18 of an endoscope light source device according to a thirteenth embodiment of this invention. This thirteenth embodiment is constructed by fitting the connector receptacle 61 with a mechanism 106 for displaying a number of rotation of the connector receptacle 61. With this thirteenth embodiment of the invention, the outer peripheral wall of the connector receptacle 61 is fitted with a surrounding gear 107, which is engaged with a larger gear 108. A pointer 110 is fitted to the central shaft 109 of the larger gear 108. The pointer 110 is on a rotation number display graduated disc 111 mounted on, for example, the front panel 18 of the light source device body 6. The rotation of the connector receptacle 61 is transmitted to the pointer 110 through the larger gear 108. The angle through which the pointer 110 is rotated displays a number of rotations of the connector receptacle 61, enabling the operator to recognize a number of rotation of the connector receptacle 61 from an indication on the graduated disc 111. Where the endoscope body 1 is expected to be rotated in either direction before a coeliac examination is made by the endoscope, the connector 5 can be connected to the connector receptacle 61, after the connector receptacle 61 is returned to the central position.

What is claimed is:

1. In an endoscope system comprising an endoscope having a light guide and an endoscope connector having a base through which said light guide passes, said light guide projecting from said base, and said endoscope connector further having contact pins and air-conducting tubes projecting from said base substantially in parallel with said light guide, the improvement comprising:

a light source device body including a fluid conducting means; and means defining a fitting cavity having a substantially cylindrical portion;

a substantially cylindrical connector receptacle having:

an outer peripheral wall;

a substantially central through hole penetrated by said light guide which passes through said base of said endoscope connector; and axial connection holes formed in said connector receptacle so as to be penetrated by respective contact pins projecting from said endoscope connector base substantially in parallel with said light guide;

said substantially cylindrical connector receptacle being rotatably received in said fitting cavity of said light source device body in a state rotatable about said central through hole of said connector receptacle;

a light source unit provided in said light source device body in a state facing said light guide when said connector receptacle is received in said fitting cavity of said light source device body;

control circuits provided in said light source device body;

first electrical connecting leads provided in said connector receptacle, and which respectively have two ends, one end of each first electrical connecting lead being connected to a corresponding contact pin when said connector receptacle is received in said fitting cavity of said light source device body;

second electrical connecting leads in said fitting cavity defining means, and which respectively have two ends, one end of each second electrical connecting lead being connected to a corresponding control circuit;

means for electrically connecting said first electrical connecting leads to respective ones of said electrical connecting leads at their other respective ends when said connector receptacle takes any desired rotated position in said fitting cavity, including:

a plurality of contact rings mounted on and extending around the outer periphery of said connector receptacle, each contact ring being connected to the other end of a corresponding respective first electrical connecting lead; and a plurality of contact strips fixed in said substantially cylindrical portion of said fitting cavity of said light source device body in a state so as to contact a corresponding respective contact ring, each contact strip being further connected to the other end of a corresponding respective second electrical connecting lead;

connection conduits in said connector receptacle, and which respectively have two ends, one of said ends thereof communicating with corresponding respective air-conducting tubes projecting from said endoscope connector base;

air passages which respectively have two ends, one of said ends thereof being connected to the other ends of corresponding respective ones of said connection circuits; and further air-conducting tubes coupling respective ones of said air passages at the respective other ends thereof, with said fluid-conducting means when said connector receptacle takes any desired rotated position in said fitting cavity, said further air-conducting tubes each having a portion of the length thereof loosely wound about an outer surface portion of said connector receptacle.

2. The endoscope light source device according to claim 1, wherein said further air-conducting tubes are respectively adjacent each other, and every adjacent further air-conducting tube is wound about said connector receptacle in mutually opposite directions.

3. The endoscope light source device according to claim 1, wherein lateral walls of the respective adjacent further air-conducting tubes are tightly juxtaposed to each other.

4. The endoscope light source device according to claim 1, wherein said cavity defining means comprises means defining a box in said endoscope light source device body for rotatably holding said connector receptacle.

5. The endoscope light source device according to claim 4, wherein said box comprises partition boards to separate each adjacent further air-conducting tube from each other.

6. The endoscope light source device according to claim 5, wherein said box has an inner wall, part of which is concentric with said cylindrical connector receptacle.

7. The endoscope light source device according to claim 6, further comprising an adjustment chamber provided in said box to adjust the extent to which said further air-conducting tubes are to be drawn out of said box.

8. The endoscope light source device according to claim 4, wherein said box has an inner wall, part of which is concentric with said cylindrical connector receptacle.

9. The endoscope light source device according to claim 8, further comprising an adjustment chamber provided in said box to adjust the extent to which said further air-conducting tubes are to be drawn out of saix box.

10. In an endoscope system comprising an endoscope having a light guide and an endoscope connector having a base through which said light guide passes, said light guide projecting from said base, and said endoscope connector further having contact pins and air-conducting tubes projecting from said base substantially in parallel with said light guide, the improvement comprising:

a light source device body including a fluid conducting means; and means defining a cavity having a substantially cylindrical portion;

a substantially cylindrical connector receptacle having:

an outer peripheral wall;

a substantially central through hole penetrated by said light guide which passes through said base of said endoscope connector; and axial connection holes formed in said connector receptacle so as to be penetrated by respective contact pins projecting from said endoscope connector base substantially in parallel with said light guide;

said substantially cylindrical connector receptacle being rotatably received in said cavity of said light source device body in a state rotatable about said central through hole of said connector receptacle;

a light source unit provided in said light source device body in a state facing said light guide when said connector receptacle is received in said cavity of said light source device body;

control circuits provided in said light source device body;

electrical connecting leads provided in said connector receptacle, and which respectively have two ends, one end of each electrical connecting lead being connected to a corresponding contact pin when said connector receptacle is received in said cavity of said light source device body;

said electrical connecting leads passing out of said connector receptacle and the other ends thereof being coupled to said control circuits external of said connector receptacle;

part of each of said electrical connecting leads loosely surrounding an outer surface portion of said connector receptacle;

connection conduits in said connector receptacle, and which respectively have two ends, one of said ends thereof communicating with corresponding respective air-conducting tubes projecting from said endoscope connector base;

air passages which respectively have two ends, one of said ends thereof being connected to the other ends of corresponding respective ones of said connection conduits; and further air-conducting tubes coupling respective ones of said air passages at the respective other ends thereof, with said fluid-conducting means when said connector receptacle takes any desired rotated positions in said cavity, said further air-conducting tubes each having a portion of the length thereof loosely surrounding an outer surface portion of said connector receptacle.

11. The endoscope light source device according to claim 1 or 10, further comprising a rotation-control mechanism in said light source device body to control the rotation of said connector receptacle.

12. The endoscope light source device according to claim 1, wherein said rotation control mechanism comprises a rotation control member fixed to said light source device body; and a pin mounted on said connector receptacle in a state capable of being pressed against the rotation control member.

13. The endoscope light source device according to claim 1 or 10, further comprising a brake mechanism in said light source device to stop the rotation of said connector receptacle.

14. The endoscope light source device according to claim 13, wherein said brake mechanism comprises:
   a pad engageable with the connector receptacle;
   a shoe for holding the pad;
   a plate-shaped follower integrally formed with the shoe;
   a cam which is rotatably provided in the light source device and coupled to the plate-shaped follower, and, when rotated, pushes the plate-shaped follower toward the connector receptacle for pressing the pad against the connector receptacle;
   a knob coupled to the cam and projecting out of the light source device body, and, when rotated, causes the cam to be rotated; and
   a spring stretched between the plate-shaped follower and the light source device body and normally urging the plate-shaped follower to cause the pad to be set apart from the connector receptacle.

15. In an endoscope system comprising an endoscope having a light guide and an endoscope connector having a base through which said light guide passes, said light guide projecting from said base, and said endoscope connector further having contact pins and air-conducting tubes projecting from said base substantially in parallel with said light guide,
   the improvement comprising:
   a light source device body including a fluid conducting means; and means defining a cavity having a substantially cylindrical portion;
   a substantially cylindrical connector receptacle having:
      an outer peripheral wall;
      a substantially central through hole penetrated by said light guide which passes through said base of said endoscope connector; and
      axial connection holes formed in said connector receptacle so as to be penetrated by respective contact pins projecting from said endoscope connector base substantially in parallel with said light guide;
   said substantially cylindrical connector receptacle being rotatably received in said cavity of said light source device body in a state rotatable about said central through hole of said connector receptacle;
   a light source unit provided in said light source device body in a state facing said light guide when said connector receptacle is received in said cavity of said light source device body;
   control circuits provided in said light source device body;
   electrical connecting leads provided in said connector receptacle, and which respectively have two ends, one end of each electrical connecting lead being connected to a corresponding contact pin when said connector receptacle is received in said cavity of said light source device body;
   control signal lines which respectively have two ends, one end of each control signal line being connected to a corresponding control circuit, and the other end of each control signal line being connected to a corresponding respective electrical connecting lead;
   connection conduits in said connector receptacle, and which respectively have two ends, one of said ends thereof communicating with corresponding respective air-conducting tubes projecting from said endoscope connector base;
   air-conducting tubes coupled at one end to corresponding respective connection conduits of said connector receptacle, said air-conducting tubes extending rearwardly of said connector receptacle for connection at the other ends thereof to said fluid conducting means;
   said control signal lines and said air-conducting tubes being knitted together rearwardly of said connector receptacle.

16. The endoscope light source device according to claim 11, wherein said rotation control mechanism comprises:
   a rotation control member fixed to the light source device body;
   a first gear rotatably provided in the light source device;
   a second gear mounted on the connector receptacle;
   an intermediate gear assembly engageable with the first and second gears; and
   a pin provided on the first gear and contacting the rotation control member in accordance with the extent of the rotation of the first gear.

17. The endoscope light source device according to claim 10, wherein said further air-conducting tubes are adjacent each other, and every adjacent further air-conducting tube is wound about said connector receptacle in mutually opposite directions.

18. The endoscope light source device according to claim 10, wherein lateral walls of all adjacent electrical connecting leads are tightly juxtaposed to each other; and lateral walls of all adjacent further air-conducting tubes are tightly juxtaposed to each other.

19. The endoscope light source device according to claim 18, wherein said cavity defining means comprises means defining a box in said endoscope light source body for rotatably holding said connector receptacle.

20. The endoscope light source device according to claim 19, wherein said box comprises partition boards to separate all of said adjacent further air-conducting tubes from each other.

21. The endoscope light source device according to claim 20, wherein said box has an inner wall, part of which is concentric with said cylindrical connector receptacle.

22. The endoscope light source device according to claim 21, further comprising an adjustment chamber provided in said box to adjust the extent to which said further air-conducting tubes are to be drawn out of said box.

23. The endoscope light source device according to claim 19, wherein said box has an inner wall, part of which is concentric with said cylindrical connector receptacle.

24. The endoscope light source device according to claim 23, further comprising an adjustment chamber provided in said box to adjust the extent to which said further air-conducting tubes are to be drawn out of said box.

25. The endoscope light source device according to claim 15, wherein said control signal lines and said air-conducting tubes are loosely knotted together rearwardly of said connector receptacle.

26. The endoscope light source device according to any one of claims 1, 10 or 15, comprising a rotation display mechanism in said light source device body and being operable interlockingly with the rotation of said connector receptacle for indicating a number of rotations of said connector receptacle relative to said light source device body.

* * * * *

UNITED STATES PATENT AND TRADEMARK OFFICE
CERTIFICATE OF CORRECTION

PATENT NO. : 4,402,313
DATED      : September 6, 1983
INVENTOR(S) : Hisao YABE

It is certified that error appears in the above-identified patent and that said Letters Patent is hereby corrected as shown below:

COLUMN 4, line 28, after "and signal lines" insert --16--;

COLUMN 8, line 42, change "leads connected" to --leads 30 are connected--;

COLUMN 8, line 43, change "and 80 are connected" to --80 and are connected--;

Signed and Sealed this

Twenty-seventh Day of March 1984

[SEAL]

Attest:

GERALD J. MOSSINGHOFF

Attesting Officer    Commissioner of Patents and Trademarks